:::: US005620002A

United States Patent [19]
Hughes

[11] Patent Number: 5,620,002
[45] Date of Patent: Apr. 15, 1997

[54] METHOD FOR CORRECTING THERMAL DRIFT IN CARDIAC OUTPUT DETERMINATION

[75] Inventor: Timothy J. Hughes, Palo Alto, Calif.

[73] Assignee: Abbott Critical Care Systems, Abbott Park, Ill.

[21] Appl. No.: 577,629

[22] Filed: Dec. 22, 1995

[51] Int. Cl.$^6$ ................................. A61B 5/02; A61B 5/00
[52] U.S. Cl. ............................................ 128/713; 128/736
[58] Field of Search ..................................... 128/713, 736

[56] References Cited

U.S. PATENT DOCUMENTS

| | | |
|---|---|---|
| 3,085,431 | 4/1963 | Yerman et al. |
| 3,359,974 | 12/1967 | Khalil. |
| 3,519,924 | 7/1970 | Burton. |
| 3,985,123 | 10/1976 | Herzlinger et al. |
| 3,988,928 | 11/1976 | Edstrom et al. |
| 4,059,982 | 11/1977 | Bowman. |
| 4,217,910 | 8/1980 | Khalil. |
| 4,236,527 | 12/1980 | Newbower et al. |
| 4,332,157 | 6/1982 | Zemel et al. |
| 4,361,049 | 11/1982 | Volgyesi. |
| 4,403,615 | 9/1983 | Hoehner. |
| 4,450,719 | 5/1984 | Nishimura et al. |
| 4,501,145 | 2/1985 | Boegli et al. |
| 4,507,974 | 4/1985 | Yelderman ........................... 73/861.06 |
| 4,542,748 | 9/1985 | Roy. |
| 4,637,253 | 1/1987 | Sekimura et al. |
| 4,672,962 | 6/1987 | Hershenson. |
| 4,679,561 | 7/1987 | Doss. |
| 4,685,470 | 8/1987 | Sekii et al. |
| 4,730,623 | 3/1988 | Lee. |

(List continued on next page.)

FOREIGN PATENT DOCUMENTS

| | | |
|---|---|---|
| 1108-331-A | 2/1981 | U.S.S.R. |
| WO91/16603 | 10/1991 | WIPO. |
| WO91/17703 | 11/1991 | WIPO. |

OTHER PUBLICATIONS

A. L. Delaunois, "Thermal Method For Continuous Blood–Velocity Measurements In Large Blood Vessels, And Cardiac–Output Determination," *Medical and Biological Engineering*, vol. 11, No. 2, (201–205) Mar. 1973.

J. H. Philip et al., "Continuous Thermal Measurement of Cardiac Output," *IEEE Transactions on Biomedical Engineering*, vol. BME–31, No. 5 (393–400) May 1984.

*Primary Examiner*—William E. Kamm
*Assistant Examiner*—Carl H. Layno
*Attorney, Agent, or Firm*—Christensen O'Connor Johnson & Kindness PLLC

[57] ABSTRACT

A method and apparatus for correcting thermal drift in cardiac output measurements based upon a temperature signal indicative of the change in temperature of blood leaving the heart is disclosed. In a first preferred embodiment of a cardiac output monitoring system (10), the catheter (14) is provided with an electrical resistance heater (22). An electrical current having a sinusoidal waveform with a period of from 30 to 60 seconds is applied to the heater, causing power to be dissipated into the blood within a patient's heart (12). A temperature sensor (24) disposed near a distal end of the catheter produces a signal indicative of the temperature of blood leaving the heart. The temperature signal and the signal corresponding to the electrical power dissipated in the heater (an input signal) are filtered at a frequency ωn corresponding to the frequency of the applied electrical current, i.e., the frequency of the input signal. An output signal indicative of the temperature of the blood leaving the heart corrected for the effects of thermal drift is then calculated. The blood temperature output signal is first split into two equal overlapping time periods. The two signals are then filtered separately to produce two partially independent output signals in the frequency domain. These two frequency domain output signals are then combined into a single corrected frequency domain output signal with the effects of thermal drift removed. The amplitude of the input power, the amplitude of the temperature signal corrected for thermal drift, and their phase difference are then used in calculating cardiac output.

28 Claims, 3 Drawing Sheets

U.S. PATENT DOCUMENTS

| | | |
|---|---|---|
| 4,745,928 | 5/1988 | Webler et al. . |
| 4,819,655 | 4/1989 | Webler . |
| 4,821,568 | 4/1989 | Kiske . |
| 4,841,981 | 6/1989 | Tanabe et al. . |
| 4,860,744 | 8/1989 | Johnson et al. . |
| 4,869,248 | 9/1989 | Narula . |
| 4,901,734 | 2/1990 | Griffin et al. . |
| 4,907,589 | 3/1990 | Cosman . |
| 4,949,724 | 8/1990 | Mahutte et al. . |
| 4,955,377 | 9/1990 | Lennox et al. . |
| 4,966,597 | 10/1990 | Cosman . |
| 4,979,514 | 12/1990 | Sekii et al. . |
| 4,979,948 | 12/1990 | Geddes et al. . |
| 4,993,420 | 2/1991 | Welkowitz et al. . |
| 5,035,514 | 7/1991 | Newman . |
| 5,046,505 | 9/1991 | Sekii et al. . |
| 5,056,526 | 10/1991 | Khalil . |
| 5,080,106 | 1/1992 | Sekii et al. . |
| 5,101,828 | 4/1992 | Welkowitz et al. . |
| 5,106,360 | 4/1992 | Ishiwara et al. . |
| 5,122,137 | 6/1992 | Lennox . |
| 5,146,414 | 9/1992 | McKown et al. ............... 128/713 |
| 5,261,411 | 11/1993 | Hughes ........................ 128/713 |
| 5,277,191 | 1/1994 | Hughes . |
| 5,285,796 | 2/1994 | Hughes . |
| 5,363,856 | 11/1994 | Hughes et al. ............... 128/713 |
| 5,474,080 | 12/1995 | Hughes . |

METHOD FOR CORRECTING THERMAL DRIFT IN CARDIAC OUTPUT DETERMINATION

FIELD OF THE INVENTION

The present invention relates to methods and apparatus for correcting for thermal drift in cardiac output determinations.

BACKGROUND OF THE INVENTION

Cardiac output, the volumetric rate at which blood is pumped through the heart, is most often determined clinically by injecting a bolus of chilled saline or glucose solution into the right auricle or right ventricle through a catheter. A thermistor disposed in the pulmonary artery is used to determine a temperature-time washout curve as the chilled injectate/blood mixture is pumped from the heart. The area under this curve provides an indication of cardiac output. Although this thermodilution method can give an indication of cardiac output at the time the procedure is performed, it cannot be used for continuously monitoring cardiac output. Moreover, the frequency with which the procedure is performed is limited by its adverse effects on a patient, including the dilution of the patient's blood that occurs each time the chilled fluid is injected. In addition, the procedure poses an infection hazard to medical staff from blood contact, and to the patient, from exposure to possibly contaminated injectate fluid or syringes.

Alternatively, blood in the heart can be chilled or heated in an injectateless method by a heat transfer process using a temperature-conditioned fluid that is pumped in a closed loop, toward the heart through one lumen within the catheter and back through another lumen. The principal advantages of using such a non-injectate heat transfer process to change the temperature of blood are that repetitive measurements can be performed without overloading the patient with large quantities of fluid or exposing the patient to the risk of infection.

U.S. Pat. No. 4,819,655 (Webler) discloses an injectateless method and apparatus for determining cardiac output. In Webler's preferred embodiment, a saline solution is chilled by a refrigeration system or ice bath and introduced into a catheter that has been inserted through a patient's cardiovascular system into the heart. The catheter extends through the right auricle and right ventricle and its distal end is disposed just outside the heart in the pulmonary artery. A pump forces the chilled saline solution through a closed loop fluid path defined by two lumens in the catheter, so that heat transfer occurs between the solution and blood within the heart through the walls of the catheter. A thermistor disposed at the distal end of the catheter monitors the temperature of blood leaving the heart, both before the chilled fluid is circulated through the catheter to define a baseline temperature, and after the temperature change in the blood due to heat transfer with the chilled saline solution has stabilized. Temperature sensors are also provided to monitor both the temperature of the chilled saline solution at or near the point where it enters the catheter (outside the patient's body) and the temperature of the fluid returning from the heart. In addition, the rate at which the chilled solution flows through the catheter is either measured or controlled to maintain it at a constant value. Cardiac output (CO) is then determined from the following equation:

$$CO = \frac{\dot{V}_I \cdot (\Delta T_I)}{C \cdot (\Delta T_B)} \quad (1)$$

where $\dot{V}_I$ equals the rate at which the chilled fluid is circulated through the catheter; $\Delta T_I$ equals the difference between the temperature of the chilled fluid input to the catheter and the temperature of the fluid returning from the heart; $\Delta T_B$ equals the difference between the temperature of the blood leaving the heart before the chilled fluid is circulated and the temperature of the blood leaving the heart after the chilled fluid is circulated (after the temperature stabilizes); and C is a constant dependent upon the blood and fluid properties. The patent also teaches that the fluid may instead be heated so that it transfers heat to the blood flowing through the heart rather than chilled to absorb heat.

U.S. Pat. No. 4,819,655 further teaches that the cardiac monitoring system induces temperature variations in the pulmonary artery that are related to the patient's respiratory cycle and are therefore periodic at the respiratory rate. Accordingly, Webler suggests that the signal indicative of $T_B'$ (the temperature of the chilled blood exiting the heart) should be processed through a Fourier transform to yield a period and amplitude for the respiratory cycle, the period or multiples of it then being used as the interval over which to process the data to determine cardiac output.

Another problem recognized by Webler is the delay between the times at which circulation of the chilled fluid begins and the temperature of the blood in the pulmonary artery reaches equilibrium, which is caused by the volume of blood surrounding the catheter in the right ventricle and in other portions of the heart. The patent suggests introducing a generally corresponding delay between the time that temperature measurements are made of the blood before the chilled fluid is circulated and after, for example, by waiting for the $T_B'$ value to exceed a level above that induced by respiratory variations. However, for a relatively large volume heart and/or very low cardiac output, the $T_B'$ data do not reach equilibrium in any reasonable period of time. The quantity of blood flowing through the large volume heart represents too much mixing volume to accommodate the technique taught by Webler for processing the data to determine cardiac output. As a result, the measurement period for equilibrium must be excessively long to reach equilibrium, thereby introducing a potential error in the result due to either a shift in the baseline temperature of the blood or changes in the cardiac output. For this reason, the technique taught by Webler to determine cardiac output using the data developed by his system is not practical in the case of large blood volumes in the heart and/or low cardiac outputs.

Instead of cooling (or heating) the blood in the heart by heat transfer with a circulating fluid to determine cardiac output, the blood can be heated with an electrical resistance heater that is disposed on a catheter inserted into the heart. The apparatus required for this type of injectateless cardiac output measurement is significantly less complex than that required for circulating a fluid through the catheter. An electrical current is applied to the resistor through leads in the catheter and adjusted to develop sufficient power dissipation to produce a desired temperature rise signal in the blood. However, care must be taken to avoid using a high power that might damage the blood by overheating it. An adequate signal-to-noise ratio is instead preferably obtained by applying the electrical current to the heater at a frequency corresponding to that of the minimum noise generated in the circulatory system, i.e., in the range of 0.02 through 0.15 Hz.

U.S. Pat. No. 4,236,527 (Newbower et al.) describes such a system, and more importantly, describes a technique for processing the signals developed by the system to compensate for the above-noted effect of the mixing volume in the heart and cardiovascular system of a patient, even one with a relatively large heart. (Also see J. H. Philip, M. C. Long, M. D., Quinn, and R. S. Newbower, "Continuous Thermal Measurement of Cardiac Output," IEEE Transactions on Biomedical Engineering, Vol. BMI 31, No. 5, May 1984.)

Newbower et al. teaches modulating the thermal energy added to the blood at two frequencies, e.g., a fundamental frequency and its harmonic, or with a square wave signal. Preferably, the fundamental frequency equals that of the minimal noise in the cardiac system. The temperature of the blood exiting the heart is monitored, producing an output signal that is filtered at the fundamental frequency to yield conventional cardiac output information. The other modulation frequency is similarly monitored and filtered at the harmonic frequency, and is used to determine a second variable affecting the transfer function between the injection of energy into the blood and the temperature of the blood in the pulmonary artery. The amplitude data developed from the dual frequency measurements allows the absolute heart output to be determined, thereby accounting for the variability of fluid capacity or mixing volume.

Newbower's technique for determining cardiac output requires the use of a model for the system represented by the effect of the input power on the blood temperature output signal. The data must be fit to the model to correct for mixing volume attenuation.

As an alternative to the model of Newbower, M. Yelderman has developed a method for reconstructing an impulse response for a cardiac output monitoring system using a pseudo random binary noise and cross-correlation technique. This method is described in U.S. Pat. No. 4,507,974. Yelderman teaches that any indicator may be introduced into the blood mass in the form of any stochastic or spread spectral process. For example, a catheter mounted heating filament can be energized with a stochastic or pseudo random input to supply a corresponding heat input signal to the blood in the heart. The vascular system impulse response obtained by downstream measurement and cross correlation with the input signal produces information that is then combined with a conservation of heat equation to measure volumetric fluid flow by integrating the area under the impulse response curve. Yelderman's method is prone to drift and noise being coupled into the reconstructed impulse response which makes accurate level detection and integration difficult.

One inaccuracy in prior art methods of determining cardiac output is due to thermal noise and thermal drift. Thermal drift is generally a very low frequency drift in the temperature of the blood in the heart and is due to physiological factors as opposed to the thermal energy introduced into the blood during cardiac output measurements.

One cause of thermal noise is the difference in temperature between the blood returning from different parts of the body. Fluctuating pressure gradients across the chest wall caused by respiration vary the volume of blood returning to the heart from organs outside the chest relative to the volume of blood returning from organs inside the chest. Blood returning from organs with a high metabolic rate such as the liver is hotter than blood returning from say the stomach while blood returning from the periphery is much colder depending partly on room temperature. As blood returns from different parts of the body, the temperature of the blood in the heart fluctuates, thus producing a thermal noise or thermal drift in cardiac output measurements. For example, the amount of blood entering the heart from the superior or inferior vena cava varies during each respiration cycle, thus changing the temperature of the blood in the heart. Also long term homeostatic control systems in the body cause long term slow fluctuations in mixed venous blood temperature as a result of adjusting the quantity of blood flowing to the periphery and varying the metabolic rate to try to maintain "core" temperature constant.

PCT patent WO 91/16603 (McKown) discloses a method that attempts to account for the effects of thermal drift on cardiac output measurements using Yelderman's cross-correlation technique. McKown assumes that, regardless of thermal noise or drift, the average power supplied to the blood over each measurement period and thus the average power measured during cardiac output measurements remains constant. Based on this assumption, McKown determines the average level of the resultant measured temperature signal over each of several adjacent measurement periods. In the preferred embodiment, McKown uses three measurement periods, thus producing three measurements of average signal level. A quadratic curve is then fit to the data produced by measurements of average signal level. The portion of the quadratic curve associated with the center measurement period is then subtracted from the measured cardiac output signal on a point-by-point basis in order to produce "zero mean" data, thus reducing the effects of thermal drift.

McKown's method of fitting a quadratic curve to the temperature signal fits three variables simultaneously to the noisy data. If the temperature signal is particularly noisy, such a quadratic fit can induce errors larger than those present in the uncompensated original signal. McKown's method requires at least two adjacent measurement periods to be completed prior to accounting for the effect of thermal drift. If the quadratic fit is inaccurate due to short term noise during one measurement period errors in output measurements due to that noisy period propagate to adjacent measurement periods as well, since the quadratic fit is repeated for each period using overlapping adjacent averages. This results in three inaccurate measurements instead of one. In addition, because McKown's method requires at least three measurement periods to be completed before cardiac output can be determined, there is a longer lag time between the occurrence of the cardiac event being measured and subsequent data output. This lag time prevents an operator from observing the cardiac output in real time, possibly affecting the patient's treatment. Due to measurement errors induced by signal-to-noise ratios and attenuation, the measurement time period can not generally be reduced much below 30 seconds. Thus, the results of a cardiac output measurement produced by the method of McKown would be delayed by an additional one and perhaps, up to two minutes after the cardiac event and the effects of transient noise would more likely be coupled into multiple measurements.

T. Hughes in U.S. Pat. No. 5,261,411 describes methods of reducing drift in cardiac output determinations by adjusting the starting point of the measurement period for each harmonic used so that the signal in the frequency domain has only a Real component of the input signal used. This is more complex to implement and can give rise to a small variable delay in update time. T. Hughes and D. Swingler in U.S. Pat. No. 5,363,856 describe methods for reducing drift in cardiac output determinations by shifting and adding the thermal signal to itself so as to leave only the drift signal and then identifying the drift slope by regression techniques. This allows drift removal within a single period of the input signal but is complex requiring robust regression techniques to be used in the presence of non-Gaussian thermal noise.

A goal of the present invention is to provide a method and apparatus for reducing the effects of thermal drift on measurements of cardiac output while reducing some of the problems associated with the prior art, including maintaining a short lag time required to determine cardiac output while minimizing the effects of noise.

SUMMARY OF THE INVENTION

The present invention corrects for the effects of thermal drift on cardiac output measurements. In one embodiment of the invention, a blood temperature output signal indicative of the temperature of the blood flowing through the heart is determined. The blood temperature output signal is split into two equal, partly overlapping time periods. The signals from these two time periods are filtered separately to produce two partially independent output signals in the frequency domain. These two frequency domain signals are combined into a single corrected frequency domain output signal with the effect of thermal drift removed. The cardiac output is then determined as a function of the output frequency domain signal with a reduced dependence on thermal drift.

In another embodiment, the cardiac output calculation is performed in the time domain. In this method, the corrected frequency domain signal is transformed back into the time domain to produce a corrected time domain output signal with a reduced dependence on thermal drift. The cardiac output is then determined as a function of the corrected time domain output signal with a reduced dependence on thermal drift.

In accordance with other aspects of the invention, the blood temperature output signal is split into two partially overlapping periods of time of T seconds each. The time delay Tdelay (in seconds) of the start of the second period of time relative to the start of the first is expressed as a phase delay of $\theta n$ (in radians) at harmonic n with angular frequency $\omega$ through equations 2–5, wherein:

$$\omega 1 = \frac{2 \cdot \pi}{T} \quad (2)$$

$$\omega n = \frac{2 \cdot \pi \cdot n}{T} \quad (3)$$

$$\text{with} \quad \theta n = \frac{-2 \cdot \pi \cdot n \cdot T\text{delay}}{T} \quad (4)$$

$$\text{or} \quad \theta n = -\omega n \cdot T\text{delay} \quad (5)$$

In accordance with other aspects of the invention, the signal in the first (current) time period is measured and transformed (filtered) into the frequency domain by a transform such as the Discrete Fourier Transform (DFT) or Fast Fourier Transform (FFT) producing a complex component An at a harmonic frequency $\omega n$ of the signal. Similarly, the signal in the second (delayed) measurement period is also measured and transformed into the frequency domain producing a complex component Bn at a signal frequency $\omega n$ in an identical manner. A corrected output signal Ancor for harmonic frequency $\omega n$ is then calculated as follows in equation 6:

$$Ancor = \frac{(Bn - An)}{\left| 2 \cdot \sin\left(\frac{\theta n}{2}\right) \right|} \cdot e^{i \cdot \left(\frac{\theta n - \pi}{2}\right)} \quad (6)$$

where:

$\theta n$ is the time delay phase difference between the measurement periods for harmonic number n, expressed in radians and calculated according to equation 5;

e is the base of the natural logarithm equal to approximately 2.718;

i is the complex operator with $i = \sqrt{-1}$;

An is the uncorrected complex component filtered at frequency $\omega n$ during the current measurement period;

Bn is the complex component filtered at frequency $\omega n$ measured during the overlapping but delayed time period;

and the reference phase for Ancor is taken relative to the current (first) measurement period.

Equation 6 can be expressed in terms of the real (Re) and the imaginary (Im) components of An and Bn as follows in equations 7–11.

$$Ancor = Re(An) + i \cdot \quad (7)$$

$$\left( Im(An) - Im(Bn) - \frac{(Re(An) - Re(Bn)) \cdot \cos(\theta n)}{\sin(\theta n)} \right)$$

In polar form Equations 8 and 9 describe the Magnitude, |Ancor| of Ancor:

$$|Ancor| = \frac{\sqrt{(Re(An) - Re(Bn))^2 + (Im(An) - Im(Bn))^2}}{\left| 2 \cdot \sin\left(\frac{\theta n}{2}\right) \right|} \quad (8)$$

or:

$$|Ancor| = \frac{\sqrt{|An|^2 + |Bn|^2 - 2 \cdot |An| \cdot |Bn| \cdot \cos(\arg(An) - \arg(Bn))}}{\left| 2 \cdot \sin\left(\frac{\theta n}{2}\right) \right|} \quad (9)$$

while equations 10 and 11 describe the Phase, $\phi ncor$ (in radians) of Ancor:

$$\phi ncor = \left( a\tan\left[ \frac{(Im(An) - Im(Bn))}{Re(An) - Re(Bn)} \right] - \frac{(\pi - \theta n)}{2} \right) \quad (10)$$

or:

$$\phi ncor = \left( \arg(Bn - An) - \frac{(\pi - \theta n)}{2} \right) \quad (11)$$

Equation 6 can thus be rewritten using equation 11 as equation 12.

$$Ancor = \left( \frac{|Bn - An|}{\left| 2 \cdot \sin\left(\frac{\theta n}{2}\right) \right|} \right) \cdot e^{i \cdot (\arg(Bn - An) - \frac{(\pi - \theta n)}{2})} \quad (12)$$

In accordance with further aspects of the invention, if a time delay of $\theta n$ equal to $-\pi/2$ is used, equation 12 may be simplified as shown in equations 13–16.

$$Ancor = Ana + Anb \cdot i \quad (13)$$

where:

i is the complex operator $i = \sqrt{-1}$;

Ana is Re(An); and

Anb is the Re(Bn).

This can also be expressed in polar form through Equations 14 to 15. The drift reduced magnitude |Ancor| of Ancor is given by equation 14, while the drift reduced phase $\phi ncor$ (in radians) of Ancor is given by equation 15.

$$|Ancor| = \sqrt{(Ana)^2 + (Anb)^2} \qquad (14)$$

$$\phi ncor = -\arctan\left(\frac{Anb}{Ana}\right) \qquad (15)$$

Which is expressed in complex exponential notation in equation 16:

$$Ancor = \sqrt{(Ana)^2 + (Anb)^2} \cdot e^{-i \cdot \arctan(\frac{Anb}{Ana})} \qquad (16)$$

where:

e is the base of the natural logarithm equal to approximately 2.718; and i is the complex operator with $i = \sqrt{-1}$.

In accordance with yet further aspects of the invention, if the blood temperature output signal uses more than one harmonic to calculate cardiac output, the drift reduction process is repeated for each harmonic. In addition, if the blood temperature output signal is to be processed in the time domain, then the drift reduced harmonic signals are combined using the inverse Fourier Transform to yield a corrected time domain blood temperature output signal.

In accordance with yet another method of the invention, the effects of drift may be removed by identifying the time domain drift slope using the difference between the drift reduced frequency domain estimate and the uncorrected frequency domain estimate and then subtracting the drift slope from the time domain blood temperature output signal Tb. The drift reduced time domain output signal Tbcorr is then processed in either the frequency or time domain to calculate cardiac output. One method of calculating the drift slope is shown in equation 17:

$$\text{Drift Slope} = [Im(Ancor) - Im(An)] \cdot \left(\frac{\omega n}{2}\right)\left(\frac{T}{N}\right) \qquad (17)$$

where:

N is the number of samples of the blood temperature output signal used during the signal measurement period of the input signal.

For the degenerate case of $\theta n$ equals to $-\pi/2$, equation 17 may be simplified to equation 18.

$$\text{Drift Slope} = [-Re(Bn) - Im(An)] \cdot \left(\frac{\omega n}{2}\right)\left(\frac{T}{N}\right) \qquad (18)$$

where:

N is the number of samples of the blood temperature output signal used during the signal measurement period of the input signal.

In accordance with other aspects of the invention, drift may be removed from the blood temperature output signal by subtracting the drift slope from the original time domain signal Tb using equations 19 and 20 to produce a reduced drift time domain signal.

$$Tb_{mean} = \frac{\sum_{k=0}^{N-1} Tb_k}{N} \qquad (19)$$

where:

Tb is a value of the blood temperature output signal;

$Tb_{mean}$ is the mean blood temperature over the whole period of the signal;

k is an index, running from 0 to N−1, established over a signal period; and

N is the number of samples of the blood temperature output signal used during the single measurement period of the input signal.

The corrected blood temperature output signal Tbcorr is then calculated in accordance with the following equation 20:

$$Tbcorr_k = Tb_k - (\text{Drift Slope}) \cdot \left[k - \frac{N}{2} + 0.5\right] - Tb_{mean} \qquad (20)$$

Any of the above forms of equations can be used to determine a corrected blood temperature output signal. Cardiac output is then determined as a function of the corrected blood temperature output signal and is thus corrected for thermal drift.

The present invention allows correction for thermal drift in the output signal to be achieved within only slightly more than one cycle of the measurement signal, typically within one and a quarter cycles. This is only slightly slower than the fastest previously described technique yet the technique is simple to implement and is robust in the presence of noise since it is applied in the frequency domain rather than the time domain. Thus, the present invention provides an operator with a measurement of cardiac output almost as fast as the fastest prior art methods and with a reduced error from noise in the presence of drift. This fast determination allows the operator to follow the cardiac event substantially on a real time basis, thus allowing the patient to be more accurately monitored during critical medical procedures.

Correction for thermal drift within only slightly more than one measurement period as provided by the present invention, prevents errors in one measurement period coupling over multiple measurement periods. In addition, the present invention uses purely narrow bandwidth frequency domain methods, thereby reducing inaccuracies introduced in the prior art methods that are produced by using time domain or time domain averaging methods which are inherently wider bandwidth techniques and hence more prone to noise and other artifacts.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
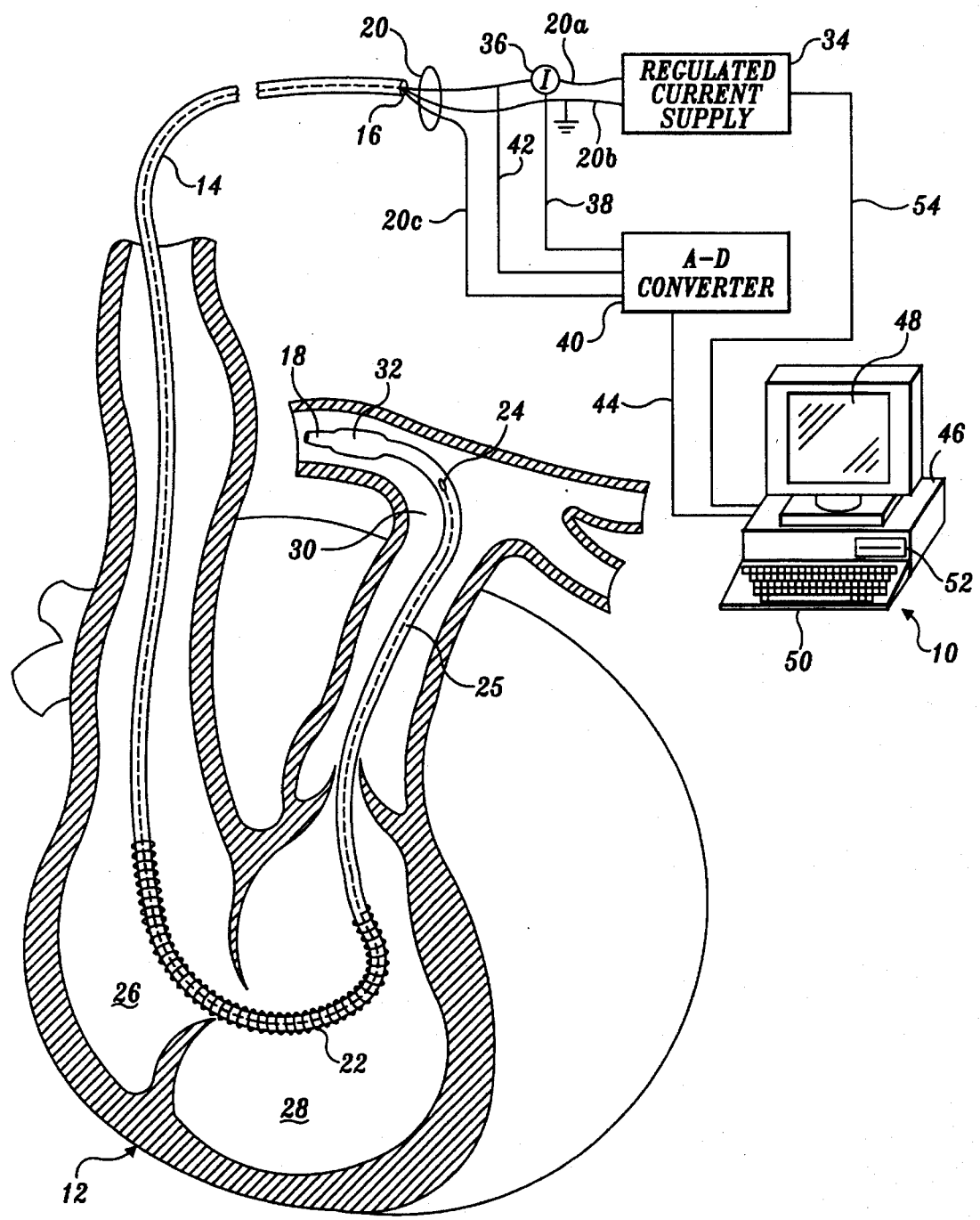
FIG. 1 is a block diagram of a first embodiment of the present invention illustrating the disposition of a catheter and electrical resistance heater within a human heart that is cut away to more clearly show the fight auricle, ventricle and pulmonary artery.

A first embodiment of a cardiac output monitoring system in accordance with the present invention is shown generally in FIG. 1 at reference numeral 10. A human heart is schematically illustrated in this figure, with a portion of the heart cut away to show the disposition of a catheter 14 that is inserted through a patient's cardiovascular system and into heart 12. Catheter 14 has a proximal end 16 and a distal end 18. A plurality of leads 20 extend longitudinally through catheter 14 (within lumens that are not separately shown) and include leads 20a and 20b that carry an electrical current to an electrical resistance heater 22.

In the preferred form of the invention, heater 22 comprises a coil of insulated copper, stainless steel, nickel, or nichrome wire approximately 12 centimeters in length that is wound around catheter 14 approximately 10 to 15 centimeters from distal end 18. Heater 22 has a nominal resistance of from 15 to 30 ohms. Leads 20c are connected to a temperature sensor 24, which is spaced apart from distal end 18 and generally mounted on the external surface of the catheter so that it can readily sense the temperature of blood flowing past the distal end as the blood is pumped from heart 12. As shown clearly in FIG. 1, catheter 14 extends through a fight auricle 26, a fight ventricle 28, and into a pulmonary artery 30 of the patient whose cardiac output is being monitored. Adjacent distal end 18 is disposed a balloon 32, which is inflated to float distal end 18 upwardly from fight ventricle 28 into pulmonary artery 30. Heater 22 can be positioned entirely within right auricle 26 or, as shown, may extend from fight auricle 26 into right ventricle 28.

A regulated current supply 34 supplies a periodic electrical current used to generate heat at heater 22, at a voltage ranging from 10 to 25 volts peak amplitude. The periodic electrical current can be supplied in a periodic waveform having either odd or even harmonics or both. Alternatively, a square wave current supply can be used. As the current flows through the wire coil comprising heater 22, it produces heat in proportion to the I²R losses in the heater (where I is the current and R is the resistance of the heater). The heat produced is transferred to the blood within fight auricle 26 and fight ventricle 28.

A current sensor 36 produces a signal indicative of the magnitude of the electrical current flowing through lead 20a to heater 22, and this signal is input through leads 38 to analog-to-digital (A-D) converters 40. A second input to A-D converters 40 is a voltage signal that indicates the voltage developed across heater 22; this voltage signal is conveyed by leads 42. The third input to the A-D converters comprises the signal indicative of the temperature of the blood leaving heart 12, produced by temperature sensor 24, connected to leads 25, which comprise the distal end of leads 20c. Digital signals from A-D converters 40 are conveyed through leads 44 to input pons (not separately shown) on a portable computer 46.

Associated with portable computer 46 is a video display 48 on which data defining the cardiac output of heart 12 are displayed, along with other data and information. A keyboard 50 is connected to portable computer 46 to provide for input and user control of the cardiac output measurement. In addition, portable computer 46 includes a hard drive or floppy drive 52 that is used for magnetic storage data, test results, and programs such as the software controlling the measurement of cardiac output. Portable computer 46 controls regulated current supply 34 by supplying control signals transmitted through leads 54 that extend between the regulated current supply and the portable computer.

Preferably, the electrical current that energizes heater 22 to heat the blood flowing through heart 12 is supplied either in the form of a sine wave having a 30 to 60 second period or a square wave with an energized period ranging between 15 and 30 seconds (followed by a like duration during which no current is supplied). The power developed by heater 22 thus represents a periodic input signal, whereas the signal developed by temperature sensor 24 comprises an output signal indicative of the temperature of the blood leaving the heart. To determine the power dissipated within heater 22, the digitized signals indicative of the current flowing through the heater and voltage drop across it are multiplied together by portable computer 46, The power dissipated within heater 22 to heat the blood flowing through heart 12, i.e., the amplitude, is therefore easily determined and is defined as the "input signal" for purposes of the following discussion. Accordingly, the power applied, which represents the input signal, and the temperature of the blood exiting the heart to the pulmonary artery, which represents the "output signal," are used in the preferred embodiment to determine the cardiac output of heart 12, as explained below.

An alternative embodiment for developing an input signal and an output signal is to convey a cooling or heating fluid to a heat exchanger formed on the catheter in a manner known in the art. In either the preferred embodiment or the alternate embodiment, whether the input signal cools the blood or heats it, the cardiac output measurement system changes the temperature of blood in the heart on a periodic basis so that the output signal produced by the temperature sensor 24 changes periodically in response thereto.

Figure 2:
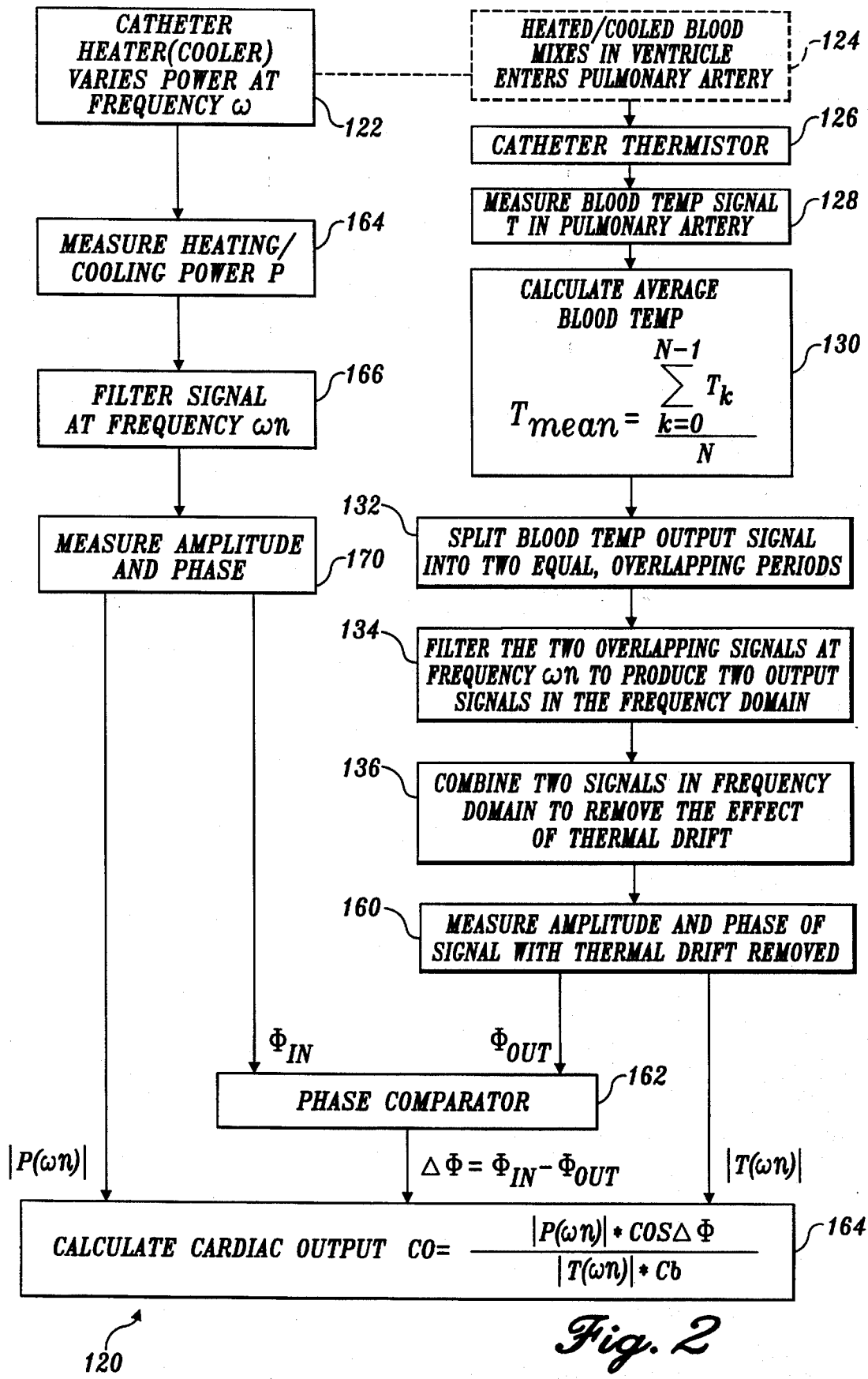
FIG. 2 is a flow chart showing the logical steps used in determining cardiac output in accordance with the present invention.

As noted in the Background of the Invention, the present invention enables cardiac output to be determined continuously, rather than intermittently and is much less prone to noise than previous continuous cardiac output monitoring methods. In the present invention, cardiac output is determined by portable computer 46 following the logic steps shown in a flow chart 120 in FIG. 2. Starting at block 122, the temperature of blood flowing through heart 12 is modified by applying the input signal, e.g., by supplying electrical current to heater 22, or by conveying a cooling fluid through the catheter, thereby modifying the temperature of blood within the heart. The transfer of heat to or from blood within the heart 12 occurs at a frequency ω, as shown in block 122.

A dashed line block 124 indicates that the blood heated or cooled by the input signal mixes with the other blood in right ventricle 28 and enters pulmonary artery 30. A block 126 refers to temperature sensor 24, which produces the signal that is indicative of the temperature of blood exiting heart 12. With reference to block 128, the blood temperature T within pulmonary artery 30 comprises the output signal that is digitized by A-D converter 40.

In blocks 130–136, the output signal is corrected for thermal drift. As indicated in block 130, the average blood temperature $Tb_{mean}$ is optionally determined by first summing the measured blood temperature T over one signal period. Since the output signal is sampled at N points, the average blood temperature over this time is determined in accordance with Equation 21 by dividing this sum by N.

$$Tb_{mean} = \frac{\sum_{k=0}^{N-1} T_k}{N} \qquad (21)$$

Figure 3:
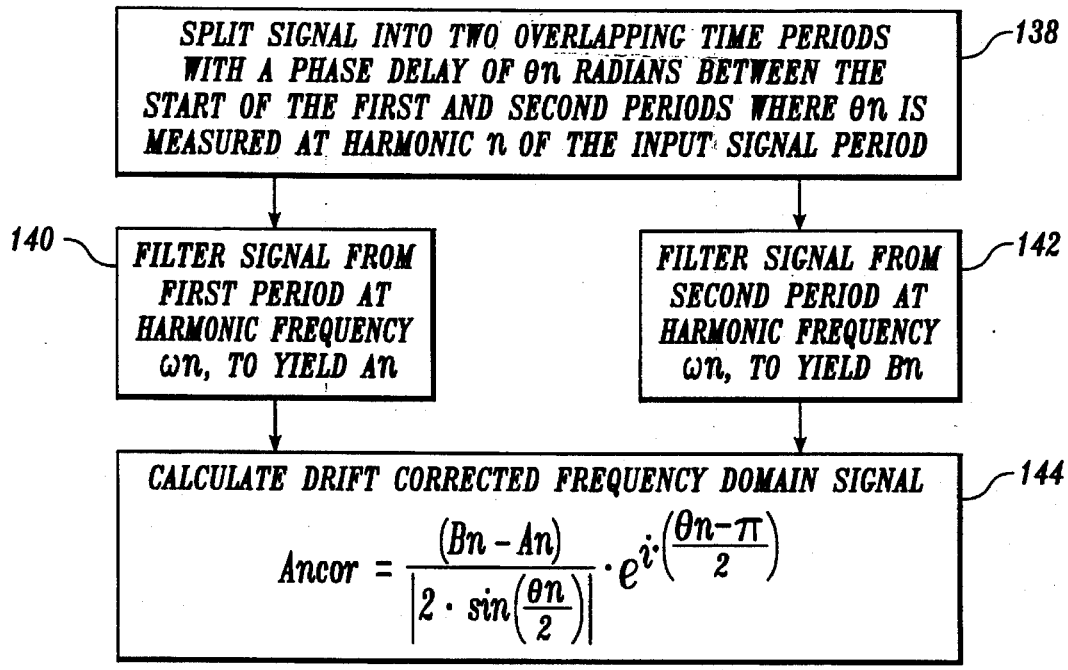
FIG. 3 is a flow chart of one method of calculating a drift corrected frequency domain signal according to the invention.
Figure 4:
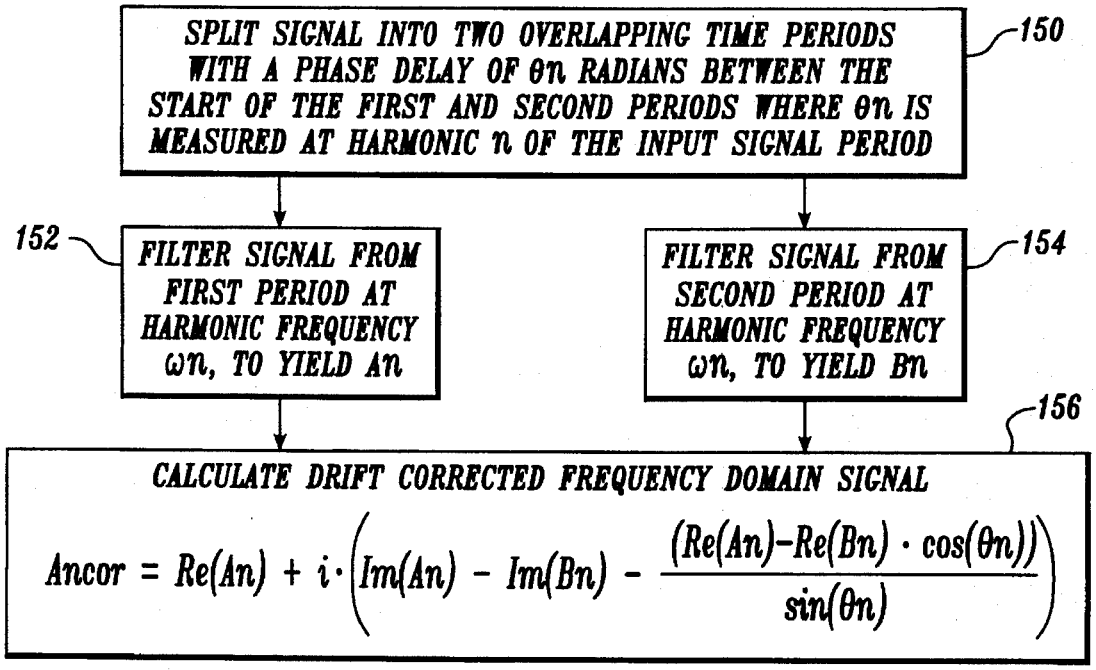
FIG. 4 is a flow chart of another method of calculating a drift corrected frequency domain signal according to the invention.

In blocks 134–136, the blood temperature output signal is split into two separate signals having equal but overlapping periods. The two overlapping signals are then filtered to produce two independent output signals in the frequency domain as shown in block 134. The two overlapping output signals are then combined in the frequency domain to remove the effects of thermal drift as shown in block 136. The method of splitting the blood temperature output signal into two equal, overlapping signals, the methods of filtering the signals and the method to combine the signals are described in more detail below with respect to FIGS. 3 and 4. FIGS. 3 and 4 further break down the method generally described above with respect to blocks 132–136.

In one preferred embodiment of the present invention illustrated in FIG. 3, the blood temperature output signal, usually a complex waveform like a square wave or pseudo random binary sequence, has a signal period of T seconds with a corresponding fundamental frequency in Radians per second of ω1 given by Equation 21.

$$\text{with} \qquad \omega 1 = \frac{2 \cdot \pi}{T} \qquad (22)$$

For any harmonic n of the fundamental frequency ω1, with n an integer, Equation 23 defines the corresponding angular frequency ω:

$$\omega n = \frac{2 \cdot \pi \cdot n}{T} \qquad (23)$$

The blood temperature output signal is split into two partially overlapping periods of time of T seconds each. The time delay Tdelay (in seconds) of the start of the second period of time relative to the start of the first can be expressed as a phase delay of θn (in radians) at harmonic n with angular frequency ω through Equations 24 and 25 as shown in blocks 138 or 150.

$$\text{with} \qquad \theta n = \frac{-2 \cdot \pi \cdot n \cdot T\text{delay}}{T} \qquad (24)$$

$$\text{or} \qquad \theta n = -\omega n \cdot T\text{delay} \qquad (25)$$

Normally θn is chosen in the range 0>θn>−2. It. The value chosen for θn is not critical with a value of −π/2 typically used for the fundamental frequency (n=1). Using −π/2 minimizes measurement response time and reduces computer burden while still providing good drift rejection. Drift and noise rejection degrade for values of θn approaching zero and for θn much larger especially between −1.5·π and −2·π. Different values of Tdelay can be used for calculating each harmonic if this is necessary to ensure phase shifts in the optimal range for each harmonic used. For convenience, a single time delay optimized for the fundamental harmonic frequency may be acceptable for use at other harmonics if the time delay phase shift at each of these harmonics falls in the optimal range, or integral multiples thereof, at the particular harmonic frequency used.

The signal in the first (current) time period is measured and transformed (filtered) into the frequency domain via a transform such as the Discrete Fourier Transform (DFT) or Fast Fourier Transform (FFT) producing a complex component An at a harmonic frequency ωn of the signal as shown in blocks 140 or 152.

The signal in the second (delayed) measurement period is also measured and transformed (filtered) into the frequency domain via a transform such as a Discrete Fourier Transform (DFT) or Fast Fourier Transform producing a complex component Bn at the signal frequency ωn in an identical manner to that used for the first measurement period as shown in blocks 142 or 154.

The two filtering operations produce estimates of the in phase (Real) components relative to each filtering window largely independent of drift because the integral of cosine multiplied by a linear drift term is zero over an integral numbers of cycles, while the Imaginary (quadrature) components have a constant error term associated with the drift. In practice, the Real component of a DFT contains a small non zero error term associated with the drift due to approximations inherent in the DFT. These error terms are common to both estimates and hence tend to cancel. By combining the two estimates at different relative times and hence different relative phases the complex drift reduced blood temperature output signal Ancor for harmonic frequency ωn is calculated as follows in Equation 26 and as shown in block 144:

$$A n c o r = \frac{(Bn - An)}{\left| 2 \cdot \sin\left(\frac{\theta n}{2}\right) \right|} \cdot e^{i \left(\frac{\theta n - \pi}{2}\right)} \qquad (26)$$

Where:

θn is the time delay phase difference between the measurement periods for harmonic number n, expressed in radians and calculated according to equation 25;

e is the base of the natural logarithm equal to approximately 2.718;

i is the complex operator with i=√−1;

An is the uncorrected complex component filtered at frequency ωn during the current measurement period;

Bn is the complex component filtered at frequency ωn measured during the overlapping but delayed time period;

and the reference phase for Ancor is taken relative to the current (first) measurement period.

The form of Equation 26 can be interpreted geometrically; the corrected measurement is the difference between the two measurements at the different time periods with a phase rotation (the exponential term) and an amplitude correction (the denominator) dependent on the time delay between the measurements.

Equation 26 can be expressed in a number of different forms based on the geometry of the corresponding phasor diagram and using standard trigonometric identities. These forms may be more convenient for a particular application. For example, using polar notation (magnitude and phase) is often a convenient form. Equation 27 expresses equation 26 in terms of the Real (Re) and Imaginary (Im) components of An and Bn as shown in block 156:

$$Ancor = Re(An) + i \cdot \qquad (27)$$

$$\left( Im(An) - Im(Bn) - \frac{(Re(An) - Re(Bn)) \cdot \cos(\theta n)}{\sin(\theta n)} \right)$$

In polar form Equations 28 and 29 describe the Magnitude, |Ancor| of Ancor:

$$|Ancor| = \frac{\sqrt{(Re(An) - Re(Bn))^2 + (Im(An) - Im(Bn))^2}}{\left| 2 \cdot \sin\left(\frac{\theta n}{2}\right) \right|} \qquad (28)$$

or:

$$|Ancor| = \frac{\sqrt{|An|^2 + |Bn|^2 - 2 \cdot |An| \cdot |Bn| \cdot \cos(\arg(An) - \arg(Bn))}}{\left| 2 \cdot \sin\left(\frac{\theta n}{2}\right) \right|} \qquad (29)$$

while equations 30 and 31 describe the Phase, φncor (in radians) of Ancor:

$$\phi n c o r = \left( a \tan \left[ \frac{(Im(An) - Im(Bn))}{Re(An) - Re(Bn)} \right] - \frac{(\pi - \theta n)}{2} \right) \qquad (30)$$

or:

$$\phi n c o r = \left( \arg(Bn - An) - \frac{(\pi - \theta n)}{2} \right) \qquad (31)$$

Equation 26 can thus be rewritten using Equation 31, as Equation 32:

$$Ancor = \left( \frac{|Bn - An|}{\left| 2 \cdot \sin\left( \frac{\theta n}{2} \right) \right|} \right) \cdot e^{i \cdot (arg(Bn - An) - \frac{(\pi - \theta n)}{2})} \quad (32)$$

A special degenerate case occurs for a time delay such that $\theta n$ equals $-\pi/2$. This simplifies the equations, minimizing the amount of calculation required. Implementing this simplified form is described as follows and summarized in equations 33 through 36:

The signal in the first (current) measurement period is measured and transformed (filtered) into the frequency domain via a Real only transform such as the Discrete Cosine Transform (DCT) or the Real only part of a Discrete Fourier Transform (DFT) producing a Real component Ana at harmonic frequency $\omega n$ of the signal.

The signal in the second (delayed) measurement period is measured and transformed (filtered) into the frequency domain via a real only transform such as the DCT or the real only part of a DFT producing a real component Anb at the signal frequency $\omega n$ in an identical manner to that used for the first measurement period.

A real only transform produces a magnitude estimate of the in phase (Real) component of the signal largely independent of drift because the integral of the cosine basis function multiplied by a linear drift term is zero over one or any integral numbers of cycles. By combining two of these Real only estimates at a phase difference of $\pi/2$ relative to one another, both the Real and Imaginary parts of the measured signal are obtained. The drift reduced complex (Real+Imaginary) frequency domain output signal Ancor for harmonic frequency $\omega n$ is given by equation 33 with the Real part coming from the first (current) measurement period and the Imaginary part coming from the second (delayed) measurement period:

$$Ancor = Ana + Anb \cdot i \quad (33)$$

where:

i is the complex operator $i = \sqrt{-1}$;

Ana is Re(An); and

Anb is the Re(Bn).

This can also be expressed in polar form through Equations 34 to 35. The drift reduced magnitude |Ancor| of Ancor is given by equation 34, while the drift reduced phase $\phi ncor$ (in radians) of Ancor is given by equation 35.

$$|Ancor| = \sqrt{(Ana)^2 + (Anb)^2} \quad (34)$$

$$\phi ncor = -\arctan\left( \frac{Anb}{Ana} \right) \quad (35)$$

Which is expressed in complex exponential notation in equation 36:

$$Ancor = \sqrt{(Ana)^2 + (Anb)^2} \cdot e^{-i \cdot \arctan(\frac{Anb}{Ana})} \quad (36)$$

where:

e is the base of the natural logarithm equal to approximately 2.718; and i is the complex operator with $i = \sqrt{-1}$.

If the blood temperature output signal calculation uses more than one harmonic to calculate cardiac output then the drift reduction process is repeated for each harmonic. If the blood temperature output signal is to be finally processed in the time domain, to calculate the cardiac output, then the drift reduced harmonic signals are combined using the Inverse Fourier Transform to yield a corrected time domain blood temperature output signal. The time domain blood temperature output signal is then used along with the input signal to calculate cardiac output.

An alternative method of removing drift involves identifying the time domain drift slope by using the difference between the drift reduced frequency domain estimate and the uncorrected frequency domain estimate and then subtracting the identified drift slope from the time domain blood temperature output signal Tb. This produces a drift reduced time domain signal Tbcorr which can then be further processed using either frequency or time domain methods to calculate cardiac output. One method of estimating this drift slope is to use the fundamental frequency signal (first harmonic) which usually contains the largest error term due to drift. Equation 37 describes this method for the most general case of any integral harmonic number n, although often only the first harmonic would be used:

$$\text{Drift Slope} = [Im(Ancor) - Im(An)] \cdot \left( \frac{\omega n}{2} \right) \left( \frac{T}{N} \right) \quad (37)$$

where:

N is the number of samples of the blood temperature output signal used during the signal measurement period of the input signal.

For the degenerate case of $\theta n$ equals $-\pi/2$ equation 37 simplifies to equation 38:

$$\text{Drift Slope} = [-Re(Bn) - Im(An)] \cdot \left( \frac{\omega n}{2} \right) \left( \frac{T}{N} \right) \quad (38)$$

where:

N is the number of samples of the blood temperature output signal used during the signal measurement period of the input signal.

Once the drift slope has been determined via equation 37 or equation 38, the drift can be removed by subtracting the drift slope from the original time domain signal Tb using equations 39 and 40 thus creating a corrected (drift reduced) time domain signal Tbcorr which may then be used to calculate the cardiac output largely independent of drift.

$$Tb_{mean} = \frac{\sum_{k=0}^{N-1} Tb_k}{N} \quad (39)$$

where:

Tb is a value of the blood temperature output signal;

$Tb_{mean}$ is the mean blood temperature over the whole period of the signal;

k is an index, running from 0 to N−1, established over a signal period; and

N is the number of samples of the blood temperature output signal used during the single measurement period of the input signal.

The corrected blood temperature output signal Tbcorr is then calculated in accordance with the following equation 40:

$$Tbcorr_k = Tb_k - (\text{Drift Slope}) \cdot \left[ k - \frac{N}{2} + 0.5 \right] - Tb_{mean} \quad (40)$$

Equation 40 removes the mean blood temperature calculated in equation 39 by subtracting $Tb_{mean}$ to help improve floating point arithmetic accuracy in many applications. This is not essential for drift removal, and $Tb_{mean}$ can be deleted from equation 40 without changing the effect of the drift removal.

After removing drift as described above, the signal can be further filtered to remove noise. For example, an analog bandpass filter circuit could be used to process the input signal before it is digitized, in lieu of the discrete Fourier transform. Other types of digital or analog filtering could also be used to eliminate noise components at other frequencies.

After the output signal is filtered, the amplitude of the filtered output signal is determined, as noted in block 160. Portable computer 46 uses the peak to peak value of the filtered output signal for this amplitude, represented by |Tb(ωn)|. The value |Tb(ωn)| is then used in a block 162 for calculating cardiac output. Since the filtered output signal is a periodically varying signal, it has a phase relationship that is represented by the value $\Phi_{out}$ (used as described below).

The left side of flow chart 120 is directed to the steps used in processing the input signal. As shown in a block 164, the power P, which represents the heat transferred to the blood in the heart, is determined. As described above, the heating power of heater 22 is determined from the product of the electrical current flowing through it and the voltage drop across the heater, as well known to those of ordinary skill in the art.

Portable computer 46 then filters the input signal at the input frequency ωn, as indicated in a block 166. To filter the input signal, the portable computer processes it with a discrete Fourier transform, converting it from the time domain to the frequency domain. The portion of the transformed signal at the frequency ωn comprises the filtered input signal. The filtered input signal has both a phase and amplitude. In a block 170, the amplitude of the input signal is determined and is input to a block 164 as |P(ωn)|. The phase of this filtered input signal, $\Phi_{in}$, is compared to the phase of the output signal in a block 162, producing a differential phase $\Delta\Phi$, which is equal to the difference between $\Phi_{in}$ and $\Phi_{out}$. Portable computer 46 determines the differential phase and as shown in block 164, calculates cardiac output "CO" as follows:

$$CO = \frac{|P(\omega n)| \cdot COS(\Delta\Phi)}{(|T_b(\omega n)| \cdot Cb)} \quad (41)$$

In the above equation 41, the value Cb is the product of specific heat and density of blood.

The volume of blood within right ventricle of heart 12, i.e., the mixing volume, is estimated from the following expression:

$$V = \frac{\tau \cdot |P(\omega n)| \sqrt{\frac{1}{(\cos(\Delta\Phi))^2} - 1}}{2 \cdot \pi \cdot Cb \cdot |T_b(\omega n)|} \quad (42)$$

where τ is the period of the input signal. To reduce the effects of phase noise on the determination of cardiac output, an estimation of mixing volume can be made from Equation 42 and used in the following relationship:

$$CO = \sqrt{\left(\left(\frac{|P(\omega n)|}{Cb \cdot |T_b(\omega n)|}\right)^2 - (\omega n \tilde{V})^2\right)} \quad (43)$$

The estimate of mixing volume is preferably averaged over a long term (assuming that volume is relatively constant over the time during which cardiac output is determined), yielding an average mixing volume, $\tilde{V}$, which is used in Equation 43 to determine cardiac output. The resulting determination of cardiac output from Equation 43 is therefore less sensitive to phase noise, including heart rate variations.

When a heat signal is injected into the blood within heart 12, either by cooling the blood or by applying heat to it, a transport delay time is incurred before the input heat signal reaches temperature sensor 24 in the pulmonary artery. The transport delay time adds a phase shift that is flow rate and vessel size dependent. The phase error due to transport delay time is defined as:

$$\Delta\Phi_{error} = \frac{\pi \cdot R^2 \cdot \omega n \cdot L}{1000 \cdot CO} \quad (44)$$

where L is equal to the length of the path from the point of which the heat signal is injected into the blood within the heart to the point at which the temperature sensor is disposed (in cm), R is the vessel radius (in cm), and CO is the cardiac output in liters/second. For example, a typical phase shift would be approximately 28.8° for a path 10 cm in length, a radius of 1.6 cm, with a rate of flow of one liter per minute, and a period for the injection of the heat signal equal to 60 seconds.

The phase shift introduced by transport delay becomes significant at relatively low flow rates, making accurate correction for the mixing volume difficult. One way to address this problem is to apply the input signal at two (or more) different frequencies, enabling a separate estimate of transport delay phase shift and mixing volume phase shift to be determined from the difference in phase shift at the different frequencies.

There are two additional sources of error for which corrections can be applied in determining cardiac output. The sources of error relate to the time constant for the catheter and thermistor caused by their respective thermal masses. The thermal mass of the catheter attenuates and phase shifts the input signal, whereas the thermal mass of temperature sensor 24 attenuates and phase shifts the received temperature signal corresponding to the change in temperature in the blood flowing past temperature sensor 24. The correction used in the preferred embodiment assumes a simple first-order system. For example, heater 22 is assumed to have a time constant $T_{htr}$ (actually the time constant is for the catheter and heater), and temperature sensor 24 to have a time constant $T_{sens}$, both of which are empirically determined. Cardiac output is then determined from:

$$CO = \frac{|P(\omega n)| \cdot COS(\Phi_{in} - \Phi_{out} - \Phi_{htr} - \Phi_{sens}) \cdot HTR_{atten} \cdot SENSOR_{atten}}{|T_b(\omega n)| \cdot Cb} \quad (45)$$

where:

$\Phi_{htr} = -ARCTAN(\omega n \cdot T_{htr})$;

$\Phi_{sens} = -ARCTAN(\omega n \cdot T_{sens})$;

$HTR_{atten} = COS(\Phi_{htr})$: and $SENSOR_{ATTEN} = COS(\Phi_{SENS})$.

Equation 45 recognizes that a time delay occurs between the arrival at temperature sensor 24 of blood having a different temperature due to the input of a heat signal and the change in the output signal of the temperature sensor. Similarly, the thermal mass of the catheter/heater introduces a time delay between the application of the input signal and the transfer of energy into the blood around heater 22 (or heat exchanger 60). Typical time constants for both heater 22 and temperature sensor 24 are approximately two seconds each. Based on the assumption that the time constants for these two elements do not vary with flow rate, amplitude errors and thus cardiac output errors introduced from this source of error should be constant, dependent only on the frequency of the input signal. Accordingly, the phase shift introduced by these time constants should also be constant. Since the sensitivity to phase errors increases at low flow rates and large mixing volumes, it is important to correct for the phase shift due to the time constants of the catheter/ heater (or heat exchanger) and temperature sensor, at large overall phase angles. A number of applications of the basic slope identification method are possible which fit a more complex curve through adjacent or overlapping measurement periods by identifying the (drift) slope of adjacent periods and then fitting a spline or higher order curve through the data using this slope information. Under high levels of noise these techniques break down and couple poor fitting errors into multiple measurement periods instead of improving accuracy. In addition they increase measurement delay time.

Trend removal as described above, is not limited to use with the cardiac output calculation method described above, but can be applied before calculation with almost any of the previously described continuous cardiac output measurement techniques including, but not limited to, those described by Yelderman (U.S. Pat. No. 4,507,974) and Newbower (U.S. Pat. No. 4,236527).

In addition, the equations presented in this patent may have to be scaled by a constant value depending on the filtering method used to convert the blood temperature output signal or power signal to the frequency domain. Although the technique described in this patent is applied after the output signal has been transformed into the frequency domain, the corrected frequency domain output signal may be transformed back into the time domain (e.g., through the Inverse Fourier Transform) after removing the drift signal at each harmonic frequency, if the cardiac output measurement calculation is normally performed in the time domain rather than the frequency domain.

While the preferred embodiment of the invention has been illustrated and described, it will be appreciated that various changes can be made therein without departing from the spirit and scope of the invention. Accordingly, it is not intended that the scope of the present invention be in any way limited by the disclosure of the preferred embodiment, but instead that it be determined entirely by reference to the claims that follow.

The embodiments of the invention in which an exclusive property or privilege is claimed are defined as follows:

1. A method for determining a cardiac output of a heart with reduced dependence on thermal drift, comprising the steps of:

(a) providing an input signal that changes a temperature of blood within the heart so that it varies periodically;

(b) sensing a temperature of blood leaving the heart, producing a blood temperature output signal that varies periodically;

(c) splitting the blood temperature output signal into two overlapping measurement time periods;

(d) producing two separate output signals in the frequency domain using the two overlapping measurement time periods;

(e) combining the two separate output signals into a single corrected frequency domain output signal with a reduced effect of thermal drift; and (f) determining cardiac output as a function of the corrected frequency domain output signal, said cardiac output thus determined having a reduced dependence on thermal drift.

2. The method of claim 1, further comprising determining a time delay phase difference $\theta n$ between a current measurement period and a delayed measurement period, expressed in radians according to:

$$\theta n = -\omega n \cdot T{delay};$$

where:
   Tdelay is the delay between the current and delayed measurement periods; and
   $\omega$ is calculated according to:

$$\omega n = \frac{2 \cdot \pi \cdot n}{T}$$

where:
   T is the signal period in seconds.

3. The method of claim 2, further comprising determining the corrected frequency domain output signal Ancor, at a harmonic n, in accordance with:

$$Ancor = \frac{(Bn - An)}{\left| 2 \cdot \sin\left(\frac{\theta n}{2}\right) \right|} \cdot e^{i\left(\frac{\theta n - \pi}{2}\right)}$$

where:
   the reference phase for Ancor is taken relative to the current measurement period;
   e is the base of the natural logarithm equal to approximately 2.718;
   i is the complex operator with $i=\sqrt{-1}$;
   An is an uncorrected complex component measured for the current measurement period; and
   Bn is an uncorrected complex component measured for the delayed measurement period.

4. The method of claim 2, further comprising determining the corrected frequency domain output signal Ancor, at harmonic n, in accordance with:

$$Ancor = Re(An) + i \cdot \left( Im(An) - Im(Bn) - \frac{(Re(An) - Re(Bn)) \cdot \cos(\theta n)}{\sin(\theta n)} \right)$$

where:
   An is an uncorrected complex component measured during the current measurement period;
   Bn is an uncorrected complex component measured during the delayed measurement period;
   Re represents the Real (in phase) component of its complex argument; and
   Im() represents the Imaginary (out of phase) component of its complex argument.

5. The method of claim 1, further comprising converting the corrected frequency domain output signal back into a corrected time domain output signal having a reduced dependence on thermal drift, and determining cardiac output as a function of the corrected time domain output signal, said cardiac output thus determined having a reduced dependence on thermal drift.

6. The method of claim 1, further comprising producing a frequency domain blood temperature output signal using the blood temperature output signal; determining a drift slope of the blood temperature output signal using the corrected frequency domain output signal and the frequency domain blood temperature output signal; subtracting the drift slope from the blood temperature output signal to produce a corrected time domain blood temperature output signal having a reduced dependence on thermal drift, and determining cardiac output as a function of the corrected time domain blood temperature output signal.

7. The method of claim 6, wherein the Drift Slope is determined in accordance with:

$$\text{Drift Slope} = [Im(Ancor) - Im(An)] \cdot \left(\frac{\omega n}{2}\right)\left(\frac{T}{N}\right)$$

where:

Ancor is the corrected frequency domain output signal;

An is the frequency domain blood temperature output signal;

$$\omega n = \frac{2 \cdot \pi \cdot n}{T}$$

where:

T is the signal period in seconds; and

N is the number of samples of the blood temperature output signal used during the signal measurement period of the input signal.

8. The method of claim 6, wherein the Drift Slope is determined in accordance with:

$$\text{Drift Slope} = [-Re(Bn) - Im(An)] \cdot \left(\frac{\omega n}{2}\right)\left(\frac{T}{N}\right)$$

where a time delay phase shift between the current measurement period and the delayed measurement period is chosen as $-\pi/2$ radians;

An is an uncorrected complex component of a current measurement period;

Bn is the complex component of an overlapping but delayed time period; and $$\omega n = \frac{2 \cdot \pi \cdot n}{T}$$

where:

T is the signal period in seconds; and

N is the number of samples of the blood temperature output signal used during the signal measurement period of the input signal.

9. The method of claim 6, wherein the corrected time domain blood temperature output signal Tbcorr is determined in accordance with:

$$Tbcorr_k = Tb_k - (\text{Drift Slope}) \cdot \left[k - \frac{N}{2} = +0.5\right]$$

where:

Drift Slope is calculated according to the method of claim 7 or claim 8;

Tb is a value of the blood temperature output signal;

k is an index, running from 0 to N−1, established over a signal period; and

N is the number of samples of the blood temperature output signal used during the single measurement period of the input signal.

10. The method of claim 2, further comprising determining the corrected frequency domain output signal Ancor in polar notation, at harmonic n, in accordance with magnitude Ancor:

$$|Ancor| = \frac{\sqrt{(Re(An) - Re(Bn))^2 + (Im(An) - Im(Bn))^2}}{\left|2 \cdot \sin\left(\frac{\theta n}{2}\right)\right|}$$

and a phase $\phi ncor$ $$\phi ncor = \left(a\tan\left[\frac{(Im(An) - Im(Bn))}{Re(An) - Re(Bn)}\right] - \frac{(\pi - \theta n)}{2}\right)$$

where:

An is an uncorrected complex component measured for a current measurement period; and Bn is an uncorrected complex component measured during a delayed measurement period.

11. The method of claim 2, further comprising determining the magnitude of the corrected frequency domain output signal Ancor at harmonic n, in accordance with:

$$|Ancor| = \frac{\sqrt{|An|^2 + |Bn|^2 - 2 \cdot |An| \cdot |Bn| \cdot \cos(\arg(An) - \arg(Bn))}}{\left|2 \cdot \sin\left(\frac{\theta n}{2}\right)\right|}$$

where:

the operation arg() represents the angle of its argument, in radians;

An is an uncorrected complex component measured for the current measurement period; and Bn is an uncorrected complex component measured for the delayed measurement period.

12. The method of claim 2, further comprising determining the phase of the corrected frequency domain output signal Ancor at harmonic n, from:

$$\phi ncor = \left(\arg(Bn - An) - \frac{(\pi - \theta n)}{2}\right)$$

where:

the operation arg() represents the angle of its argument, in radians;

An is an uncorrected complex component measured for the current measurement period; and Bn is an uncorrected complex component measured for the delayed measurement period.

13. The method of claim 2, further comprising determining the corrected frequency domain signal Ancor, at harmonic n, from:

$$Ancor = \left(\frac{|Bn - An|}{\left|2 \cdot \sin\left(\frac{\theta n}{2}\right)\right|}\right) \cdot e^{i \cdot (\arg(Bn - An) - \frac{(\pi - \theta n)}{2})};$$

where:

An is an uncorrected complex component measured for the current measurement period;

Bn is an uncorrected complex component measured for the delayed measurement period; and the operation Arg() represents the angle of its argument, in radians.

14. The method of claim 1, further comprising determining the corrected frequency domain output signal Ancor, at harmonic n, in accordance with:

$$Ancor = Re(An) + Re(Bn) \cdot i$$

where:

An is an uncorrected complex component measured during the current measurement period;

Bn is an uncorrected complex component measured for the delayed measurement period; and the time delay phase shift between the current measurement period and the delayed measurement period is chosen as $-\pi/2$.

15. Apparatus for determining a cardiac output of a heart with reduced dependence on thermal drift, comprising:

(a) a catheter that is insertable into a heart through a cardiovascular system;

(b) means for supplying a periodically varying, temperature modifying input signal to a portion of the catheter inserted into the heart;

(c) a blood temperature sensor disposed adjacent a distal end of the catheter, said temperature sensor being provided to produce a blood temperature output signal that is indicative of a temperature of blood flowing from the heart;

(d) means for compensating for thermal drift of the blood temperature output signal, by splitting the blood temperature output signal into two overlapping measurement time periods and producing two separate output signals in the frequency domain using the two overlapping measurement time periods and then combining the two separate output signals into a single corrected frequency domain output signal with a reduced effect of thermal drift; and (e) control means for determining the cardiac output of the heart as a function of said corrected frequency domain output signal, said cardiac output thus determined having a reduced dependence on thermal drift.

16. The apparatus of claim 15, further comprising means for determining time delay phase difference θn between a current measurement period and a delayed measurement period, expressed in radians and calculated according to:

$$\theta n = -\omega n \cdot Tdelay;$$

where:

Tdelay is the delay between the current and delayed measurement periods; and

ω is calculated according to:

$$\omega n = \frac{2 \cdot \pi \cdot n}{T}$$

where:

T is the signal period in seconds.

17. The apparatus of claim 16, further comprising means for determining the corrected frequency domain signal Ancor, at a harmonic n, in accordance with:

$$Ancor = \left( \frac{(Bn - An)}{\left| 2 \cdot \sin\left(\frac{\theta n}{2}\right) \right|} \right) \cdot e^{i \cdot \left(\frac{\theta n - \pi}{2}\right)}$$

where:

the reference phase for Ancor is taken relative to the current measurement period;

e is the base of the natural logarithm equal to approximately 2.718;

i is the complex operator with $i = \sqrt{-1}$;

An is an uncorrected complex component measured for the current measurement period; and Bn is an uncorrected complex component measured for the delayed second/measurement period.

18. The apparatus of claim 16, further comprising means for determining the corrected frequency domain signal Ancor, at harmonic n, in accordance with:

$$Ancor = Re(An) + i \cdot \left( Im(An) - Im(Bn) - \frac{(Re(An) - Re(Bn) \cdot \cos(\theta n))}{\sin(\theta n)} \right)$$

where:

An is an uncorrected complex component measured during the current measurement period;

Bn is an uncorrected complex component measured during the delayed measurement period;

Re represents the Real (in phase) component of its complex argument; and

Im() represents the Imaginary (out of phase) component of its complex argument.

19. The apparatus of claim 15, further comprising means for converting the corrected frequency domain output signal back into a corrected time domain output signal having a reduced dependence on thermal drift; and means for determining cardiac output as a function of the corrected time domain output signal, said cardiac output thus determined having a reduced dependence on thermal drift.

20. The apparatus of claim 15, further comprising means for producing a frequency domain blood temperature output signal using the blood temperature output signal; and determining a drift slope of blood temperature output signal using the corrected frequency domain output signal and the frequency domain blood temperature output signal; and subtracting the drift slope from the blood temperature output signal to produce a corrected time domain blood temperature output signal having a reduced dependence on thermal drift; and for determining cardiac output as a function of the corrected time domain blood temperature output signal.

21. The apparatus of claim 20, further comprising means for determining the Drift Slope in accordance with:

$$\text{Drift Slope} = [Im(Ancor) - Im(An)] \cdot \left( \frac{\omega n}{2} \right) \left( \frac{T}{N} \right)$$

where:

Ancor is the corrected frequency domain output signal;

An is the frequency domain blood temperature output signal;

$$\omega n = \frac{2 \cdot \pi \cdot n}{T}$$

where:

T is the signal period in seconds; and

N is the number of samples of the blood temperature output signal used during the signal measurement period of the input signal.

22. The apparatus of claim 20, further comprising means for determining the Drift Slope in accordance with:

$$\text{Drift Slope} = [-Re(Bn) - Im(An)] \cdot \left( \frac{\omega n}{2} \right) \left( \frac{T}{N} \right)$$

where:

N is the number of samples of the blood temperature output signal used during the signal measurement period of the input signal;

time delay phase shift between the current measurement period and the delayed measurement period is chosen as $-\pi/2$ radians;

An is an uncorrected complex component of a current measurement period;

Bn is the complex component of an overlapping but delayed time period; and $$\omega n = \frac{2 \cdot \pi \cdot n}{T}$$

where:

T is the signal period in seconds.

23. The apparatus of claim 20 further comprising means for determining the corrected time domain blood temperature output signal Tbcorr in accordance with:

$$Tbcorr_k = Tb_k - (\text{Drift Slope}) \cdot \left[ k - \frac{N}{2} = +0.5 \right]$$

where:

Drift Slope is calculated according to claim 21 or claim 22;

Tb is a value of the blood temperature output signal;

k is an index, running from 0 to N−1, established over a signal period; and

N is the number of samples of the blood temperature output signal used during the single measurement period of the input signal.

24. The apparatus of claim 16, further comprising means for determining the corrected frequency domain output signal Ancor in polar notation, at harmonic n, in accordance with:

$$|Ancor| = \frac{\sqrt{(Re(An) - Re(Bn))^2 + (Im(An) - Im(Bn))^2}}{\left| 2 \cdot \sin\left(\frac{\theta n}{2}\right) \right|}$$

$$\phi ncor = \left( atan\left[ \frac{(Im(An) - Im(Bn))}{Re(An) - Re(Bn)} \right] - \frac{(\pi - \theta n)}{2} \right)$$

where:

An is an uncorrected complex component measured for the current measurement period; and Bn is an uncorrected complex component measured during the delayed measurement period.

25. The apparatus of claim 16, further comprising means for determining the magnitude of the corrected frequency domain output signal Ancor at harmonic n, in accordance with:

$$|Ancor| = \frac{\sqrt{|An|^2 + |Bn|^2 - 2 \cdot |An| \cdot |Bn| \cdot \cos(arg(An) - arg(Bn))}}{\left| 2 \cdot \sin\left(\frac{\theta n}{2}\right) \right|}$$

where:

the operation arg() represents the angle of its argument, in radians;

An is an uncorrected complex component measured for the current measurement period; and Bn is an uncorrected complex component measured for the delayed measurement.

26. The apparatus of claim 15, further comprising means for determining the phase of the corrected frequency domain output signal Ancor at harmonic n, in accordance with:

$$\phi ncor = \left( arg(Bn - An) - \frac{(\pi - \theta n)}{2} \right)$$

where:

the operation arg() represents the angle of its argument, in radians;

An is an uncorrected complex component measured for the current measurement period; and Bn is an uncorrected complex component measured for the delayed measurement.

27. The apparatus of claim 16, further comprising means for determining the corrected frequency domain signal Ancor, at harmonic n, from:

$$Ancor = \left( \frac{|Bn - An|}{\left| 2 \cdot \sin\left(\frac{\theta n}{2}\right) \right|} \right) \cdot e^{i \cdot (arg(Bn - An) - \frac{(\pi - \theta n)}{2})};$$

where:

An is an uncorrected complex component measured for the current measurement period;

Bn is an uncorrected complex component measured for the delayed measurement period; and the operation Arg() represents the angle of its argument, in radians.

28. The apparatus of claim 15, further comprising means for determining the corrected frequency domain output signal Ancor, at harmonic n, in accordance with;

$$Ancor = Re(An) + Re(Bn) \cdot i$$

where:

An is an uncorrected complex component measured during the current measurement period;

Bn is an uncorrected complex component measured for the delayed measurement period; and the time delay phase shift between the current measurement period and the delayed measurement period is chosen as $-\pi/2$.

* * * * *